United States Patent
Deveney et al.

(10) Patent No.: US 6,874,365 B2
(45) Date of Patent: Apr. 5, 2005

(54) METHOD, SYSTEM, AND MEANS FOR ULTRASOUND INSPECTION

(75) Inventors: Kevin Paul Deveney, West Newbury, MA (US); William Evan McCormack, West Chester, OH (US); Richard Scott Chennell, Liberty Township, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/683,743

(22) Filed: Feb. 8, 2002

(65) Prior Publication Data

US 2003/0150271 A1 Aug. 14, 2003

(51) Int. Cl.⁷ ............................................. G01N 29/20
(52) U.S. Cl. ........................... 73/600; 73/599; 73/602; 73/646
(58) Field of Search .................... 73/579, 597, 598, 73/599, 600, 602, 588, 627, 646

(56) References Cited

U.S. PATENT DOCUMENTS

| | | | | |
|---|---|---|---|---|
| 4,089,225 A | * | 5/1978 | Kraska et al. ................ | 73/614 |
| 4,457,174 A | * | 7/1984 | Bar-Cohen et al. ........... | 73/598 |
| 4,794,545 A | * | 12/1988 | Salvado ....................... | 702/30 |
| 4,961,346 A | * | 10/1990 | Salvado et al. ............... | 73/644 |
| 5,170,367 A | * | 12/1992 | Mackay et al. ............... | 702/22 |
| 5,335,184 A | * | 8/1994 | Hildebrand .................. | 702/34 |
| 5,431,053 A | * | 7/1995 | Fink ............................ | 73/602 |
| 5,549,002 A | | 8/1996 | Howard et al. ............... | 73/602 |
| 5,631,424 A | | 5/1997 | Nieters et al. ................ | 73/598 |
| 5,760,904 A | | 6/1998 | Lorraine et al. ............. | 356/360 |
| 5,915,277 A | | 6/1999 | Patton ......................... | 73/601 |
| 5,974,886 A | | 11/1999 | Carroll et al. ................ | 73/598 |
| 6,099,471 A | | 8/2000 | Torp et al. ................... | 600/438 |
| 6,137,853 A | | 10/2000 | Duckering et al. .......... | 376/252 |
| 6,142,019 A | | 11/2000 | Venchiarutti et al. ........ | 73/602 |
| 6,164,136 A | * | 12/2000 | Hirsekorn et al. ........... | 73/602 |
| 6,182,512 B1 | | 2/2001 | Lorraine ..................... | 73/655 |
| 2002/0112540 A1 | * | 8/2002 | Zeroug et al. ................ | 73/579 |

FOREIGN PATENT DOCUMENTS

RU    SU 1322138 A    *    7/1987    .......... G01N/29/00

OTHER PUBLICATIONS

D.T. Hayford, E.G. Henneke, II, and W.W. Stinchcomb, "The Correlation of Ultrasonic Attenuation and Shear Strength in Graphite–Polymide Composites", Oct. 1977, Journal of Composite Materials, vol.11, pp 429–444.*

* cited by examiner

Primary Examiner—Hezron Williams
Assistant Examiner—Rose M. Miller
(74) Attorney, Agent, or Firm—William Scott Andes; Armstrong Teasdale LLP

(57) ABSTRACT

A method of ultrasound inspection is provided. The method includes providing a composite first part, introducing ultrasound to the part, receiving reflections of the ultrasound introduced in the first part, and predicting a residual strength of the first part using an amplitude of the received reflections.

11 Claims, 1 Drawing Sheet

METHOD, SYSTEM, AND MEANS FOR ULTRASOUND INSPECTION

STATEMENT REGARDING FEDERALLY SPONSORED RESEARCH & DEVELOPMENT

The government has rights in this invention pursuant to Contract No. N00019-98-C-0007 awarded by the Department of the Navy.

BACKGROUND OF INVENTION

This invention relates generally to non-destructive testing and, more particularly, to ultrasound inspection of composite parts.

Ultrasonic inspection techniques are used in many applications where non-destructive evaluation of a workpiece is required. One application of such ultrasonic inspection is in the inspection of composite fiber reinforced aircraft propeller blades. Such blades are typically formed from a plurality of layers of composite fibers (graphite, boron or S-glass, for example) laid over each other and adhesively bonded. Any separation of the fiber layers due to an incomplete bond or void in the blade may detrimentally affect blade strength. Ultrasonic inspection techniques can be used to identify and locate such flaws in a composite fiber reinforced blade. Additionally, ultrasound inspection techniques can be used to inspect composite aircraft engine parts, such as, but not limited to, composite ducts.

One technique of ultrasound inspection is sometimes referred to as bottom echo detection. By measuring the part thickness and knowing the attenuation characteristics of the part being inspected, one can compute an expected arrival time for the echo. If the echo is received earlier than expected then the ultrasound sound wave encountered an interface causing a reflection of the sound wave. This early reflection is typically caused by a delamination of the lamination layers indicating a flaw in the object. An echo received at the expected time is indicative of an absence of a delamination. This technique, however, relays on the absence or presence of the echoed sound wave and is therefore commonly called a "go/no go" type of inspection. At least one disadvantage of using a "go/no go" type of inspection is that small micro-cracks may be undetected.

SUMMARY OF INVENTION

In one aspect, a method of ultrasound inspection is provided. The method comprises providing a composite first part, introducing ultrasound to the part, receiving reflections of the ultrasound introduced in the first part, and predicting a residual strength of the part using an amplitude of the received reflections.

In another aspect, an ultrasound inspection system comprises a pulse echo transducer, and a processor operationally coupled to the transducer. The processor is configured to predict a residual strength of a first part using an amplitude of a received ultrasound reflection.

In a further aspect, an ultrasound inspection device comprises means for non-destructively testing a first part, and means for predicting a residual strength of the first part using a result from a non-destructive test of the first part with a plurality of destructive and non-destructive tests on second parts substantially similar to the first part.

DETAILED DESCRIPTION

Figure 1:
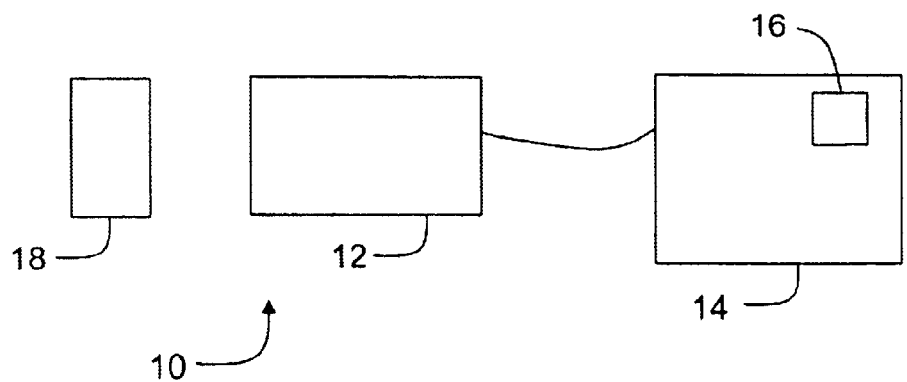
FIG. 1 is a schematic view of an ultrasound system.

FIG. 1 is a schematic view of an ultrasound system 10. System 10 includes a pulse echo transducer 12 coupled to a control unit 14 containing a processor 16. Processor 16 is configured to perform the below described processes. As used herein, the term processor is not limited to just those integrated circuits referred to in the art as processors, but broadly refers to computers, processors, microcontrollers, microcomputers, programmable logic controllers, application specific integrated circuits, and other programmable circuits.

In use, transducer 12 is placed in acoustical conduct with a part 18 to be tested and ultrasound is introduced to part 18. In one embodiment, a known acoustic gel is placed between part 18 and transducer 12 to facilitate sound transfer between part 18 and transducer 12. In another embodiment, part 18 and transducer 12 are placed proximate each other submerged in a liquid that facilitates ultrasound wave travel through the liquid. In an exemplary embodiment using the liquid in an automated setting, system 10 includes a rotatable table (not shown) including at least one collet or mandrel (not shown). Part 18 is automatically chucked in the collet or onto the mandrel and the table is rotated such that part 18 is in close proximity to transducer 12. Transducer 12 emits ultrasonic energy which is at least partially reflected when an interface is encountered within part 18 (such as a micro-crack) or at an interface on a back side of part 18 between part 18 and the liquid. Traditionally, it is the presence or absence of the reflection arising out of reaching the back side (commonly called a backside signal) that is used to determine if part 18 is structurally sound. Given the width of part 18, a window of time for the expected return of the emitted ultrasound energy is determined and if the backside signal is received within that window then part 18 is deemed structurally sound. The table is rotated and part 18 is ejected into a good part bin or a bad part bin depending on the presence or absence of the backside signal.

However, determining the presence or absence of the backside signal only reveals the presence or absence of a delamination within part 18. Accordingly, a part is kept in service until a delamination is detected. However, as explained in greater detail below, by examining an amplitude of the backside signal, a prediction of a residual shear strength can be made and the part removed from service when a likelihood of a material degradation is high regardless of whether a delamination is present.

Figure 2:
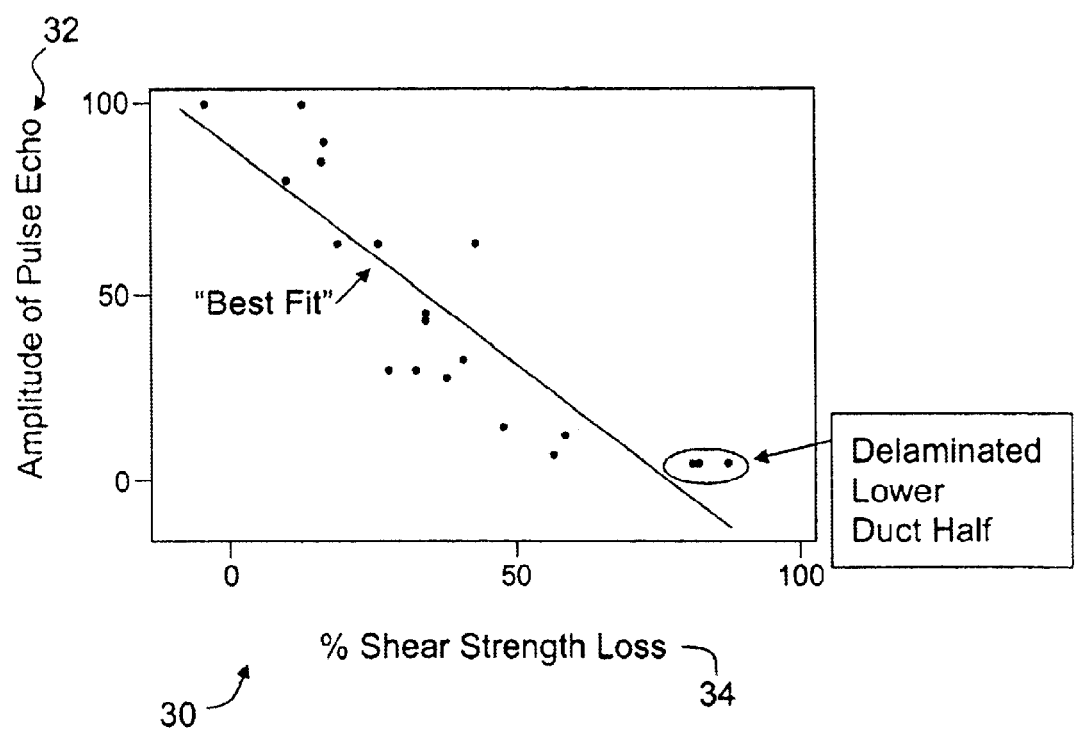
FIG. 2 is a chart illustrating a correlation of the amplitude of the backside signal with a shear strength loss for a plurality of composite parts.

FIG. 2 is a chart 30 illustrating a correlation of an amplitude 32 of the backside signal with a shear strength loss 34 for a plurality of composite parts such as composite aircraft engine parts. The parts are inspected using ultrasound system 10 (shown in FIG. 1) and using another type of inspection method. In one embodiment, the parts are inspected using a destructive test such as a core sample test wherein a core sample is removed from the part and the core is examined for micro-cracks. The results of the ultrasound test and the core sample test are correlated to provide an ability to predict a residual shear strength in a part which is only tested using ultrasound system 10. More specifically, the parts are tested ultrasonically and an amplitude of a received backside signal is correlated with results from the core-sample test. In one embodiment, the correlation is a linear least squares fit. In another embodiment, the correlation is other than a linear least squares fit.

After the correlation between the composite part's reflected backside signal and at least one non-ultrasound test of the residual strength of the parts, a part such as part 18 is tested and an amplitude of a backside signal of part 18 is obtained by using system 10. The obtained amplitude is used with the correlation to predict the residual shear strength of part 18. For example, when part 18 has an amplitude of about fifteen then, as seen in FIG. 2, the corresponding percent of shear strength loss is about sixty percent. If desired, a cut off percent is determined and when a part is predicted to have a shear strength loss greater than the cut off percent, then the part is tested further, such as performing a core sample on that part. In one embodiment, system 10 includes a memory (not shown) in which the correlation is stored, and processor 16 compares the amplitude to the stored correlation to predict a residual strength of part 18. In an exemplary embodiment, the residual strength is a residual shear strength.

While the invention has been described in terms of various specific embodiments, those skilled in the art will recognize that the invention can be practiced with modification within the spirit and scope of the claims.

What is claimed is:

1. A method of ultrasound inspection, said method comprising:
   providing a composite first aircraft engine part;
   introducing ultrasound to the first aircraft engine part;
   receiving a first set of at least one reflection of the ultrasound introduced to the first aircraft engine part;
   predicting a residual strength of the first aircraft engine part by using an amplitude of the received reflection with a plurality of results from a destructive and a non-destructive test performed on a plurality of second aircraft engine parts separate from the at least one first aircraft engine part, wherein said predicting a residual strength is performed by correlating a plurality of amplitudes of a second set of received reflections of the second aircraft engine parts with at least one non-ultrasound test of each of the second aircraft engine parts, wherein said correlating the plurality of amplitudes comprises generating a linear least squares fit between the amplitudes and a plurality of results from the non-ultrasound tests.

2. A method according to claim 1 wherein said correlating the plurality of amplitudes comprises correlating the amplitudes of the received reflections within the second set with at least one destructive test of the second aircraft engine parts.

3. A method according to claim 2 wherein said correlating the plurality of amplitudes comprises correlating the amplitudes of the received reflections within the second set with a core sample test of the second aircraft engine parts.

4. A method according to claim 1 wherein predicting a residual strength comprises predicting a residual shear strength of the first aircraft engine part using an amplitude of the at least one received reflection within the first set.

5. A method according to claim 1 wherein said correlating the plurality of the amplitudes comprises correlating the amplitudes of the received reflections within the second set with at least one non-ultrasound shear strength test of each of the second aircraft engine parts.

6. A method according to claim 1 wherein said generating the linear least squares fit comprises generating a linear least squares fit between the amplitudes and a plurality of results from at least one non-ultrasound shear strength test.

7. A ultrasound inspection system comprising:
   a pulse echo transducer;
   a processor operationally coupled to said transducer, said processor configured to predict a residual strength of a first aircraft engine part using an amplitude of a received ultrasound reflection; and
   a memory containing a correlation of a plurality of amplitudes of received reflections of a plurality of second aircraft engine parts separate from the first aircraft engine part with a plurality of results from at least one non-ultrasound test of each of the second aircraft engine parts, said processor further configured to predict a residual strength of the first aircraft engine part by using an amplitude of a received ultrasound reflection and the correlation, said memory further contains a linear least squares fit between the amplitudes and the results from the at least one non-ultrasound test.

8. A system according to claim 7 wherein the at least one non-ultrasound test includes at least one destructive test.

9. A system according to claim 7 wherein the at least one non-ultrasound test includes a core sample test.

10. A system according to claim 7 wherein the residual strength includes a residual shear strength of the first aircraft engine part.

11. An ultrasound inspection device comprising:
    means for non-destructively testing a first aircraft engine part; and
    means for predicting a residual strength of the first aircraft engine part by using a result from a non-destructive test of the first aircraft engine part with a plurality of results from destructive and non-destructive tests performed on second aircraft engine parts substantially similar to and separate from the first part, wherein said means for predicting predicts the residual strength by correlating a plurality of amplitudes of received reflections from the second aircraft engine parts with at least one non-ultrasound test of each of the second aircraft engine parts, and said means for predicting correlates the amplitudes by generating a linear least squares fit between the amplitudes and a plurality of results from the non-ultrasound tests.

* * * * *